(12) United States Patent
Nitabach

(10) Patent No.: US 6,399,360 B1
(45) Date of Patent: Jun. 4, 2002

(54) APPARATUS AND METHOD FOR MANUFACTURING ELECTROPHYSIOLOGY HARPS

(76) Inventor: Michael Nathan Nitabach, 300 E. 56th St. Apartment 3H, New York, NY (US) 10022

( * ) Notice: Subject to any disclaimer, the term of this patent is extended or adjusted under 35 U.S.C. 154(b) by 49 days.

(21) Appl. No.: 09/679,835

(22) Filed: Oct. 5, 2000

(51) Int. Cl.[7] .................................................. C12M 1/00
(52) U.S. Cl. ...................................... 435/283.1; 422/99
(58) Field of Search ........................... 435/283.1, 287.1, 435/288.3, 305.1, 305.4, 307.1, 809; 422/104, 99

(56) References Cited

PUBLICATIONS

Warner Instrument Corporation, "New Products and Product Profiles", Web–Page from On–Line Catalog, pp. 5, 7, printed on Oct. 3, 2000.

Warner Instrument Corporation, "Recording Chambers for Tissue Slice", Web–Page from On–Line Catalog, p. 1, printed on Oct. 3, 2000.

Primary Examiner—William H. Beisner

(57) ABSTRACT

The present invention comprises a jig for the manufacture of electrophysiology harps containing a top surface upon which may be placed one or more "U"s and two arrays of strand-securing notches, wherein the arrays of notches are situated one on each of two opposing edges of the top surface of the jig. Also consistent with the present invention is a method for the manufacture of electrophysiology harps exhibiting the steps of placing "U"s on the top surface of such a jig, stringing one or more strands across the "U"s such that points of contact form between the strands and the "U"s, securing the strands in the notches, cementing the points of contact, and severing the strands just distal to the points of contact. Additionally consistent with the present invention is an electrophysiology harp with strands that are substantially parallel to one another and/or equidistant from one another.

7 Claims, 3 Drawing Sheets

APPARATUS AND METHOD FOR MANUFACTURING ELECTROPHYSIOLOGY HARPS

BACKGROUND OF THE INVENTION

1. Field of the Invention

This invention relates to a method and apparatus for manufacturing miniature harps utilized to secure slices of vertebrate brain to the bottom of a recording chamber during electrophysiological recordings.

2. Description of the Related Art

Please refer to FIG. 1 "Prior Art" for the following explanation of the related art. Electrophysiological recording from vertebrate brain neurons and glial cells in semi-intact brain slice preparations is a well-established technique in modern neuroscience. Slices 50 having a thickness t of approximately 0.1 mm, and ranging from roughly 1 to 3 mm in diameter d, are cut (using a razor blade mounted on a "vibratome") from living brain tissue that has been acutely dissected from a vertebrate animal. Such a slice 50 is placed in a recording chamber under a compound microscope so that the neurons and glia, as well as the tip of the electrode, can be seen during the course of electrophysiological recording. In order to keep the neurons and glia in the tissue slice alive, and to allow for the introduction of pharmacological agents, oxygenated saline solution continuously flows through the chamber.

Unless the slice of brain tissue is secured in some fashion to the bottom of the recording chamber, the flow of saline would cause the slice to drift and otherwise move in the chamber. This makes it impossible to obtain successful electrophysiological recordings from neurons or glia in the slice. However, the use of miniature harps to secure the brain slice to the bottom of the recording chamber is well known in the art.

The harp 100 is a "U"-shaped piece of flattened metal wire 10 that has been strung between the arms 20a,b parallel to the base of the "U" 30 with the separated strands 40 of woven synthetic fiber dental floss. The strands 40 are strung at a spacing s of roughly 1 mm. The "U" 10 is of a width W and a length L that when laid flat, a brain slice 50 such as described above can be completely surrounded on three sides by the "U". In other words, the brain slice is inside the "U". When the harp is laid atop the brain slice, the strands of dental floss transfer some of the weight of the metal "U" onto the slice, thereby securing it to the bottom of the recording chamber. Because the strands of dental floss have some flexibility, not all of the weight of the "U" is borne by the brain slice—some of it is borne by the bottom of the recording chamber.

Such harps are constructed one-by-one by hand, in a tedious and painstaking procedure as follows. A piece of wire, approximately 0.2 mm in diameter, made from a heavy and relatively non-reactive metal such as platinum is cut to a length of approximately 30 mm. This piece of wire is then bent into a squared "U" shape, with each arm of the "U" being approximately 10 mm in length. Then, the "U" is hammered flat, so that one flattened side of the wire will touch the bottom of the recording chamber when the completed harp is laid therein, and the other flattened side faces directly upwards.

The flattened metal "U" is then pushed into a wide horizontal platform fashioned from modeling clay, so that the "U" is lying down in the clay in the same configuration as if it were lying down in the recording chamber. Separated strands of dental floss are then strung across the "U", parallel to the open edge and with a roughly 1 mm spacing between each strand. The ends of each strand are temporarily secured by pressing them into the modeling clay that surrounds the "U". Once all of the necessary number of strands (usually 5–10) have been temporarily secured, a tiny droplet of quick-drying "superglue"-type cement is applied to each of the two points of contact between each strand of dental floss and the metal "U". Once the glue has dried, the strands are severed just distal to their glued contacts with the metal "U", and the resulting completed electrophysiology harp can be removed from the modeling clay platform and put to its intended use.

The aspect of this prior-art method of manufacture of electrophysiology harps that is most tedious and potentially frustrating to the electrophysiologist is the stringing of the separated dental floss strands across the arms of the "U", and temporarily securing them by pressing them into the modeling clay. This aspect of the procedure is by far the most time-consuming. The separated strands, because they are so thin, must be manipulated with small forceps. Frequently, as one strand is being temporarily secured by pressing into the clay, other, already temporarily secured, strands are being displaced. Indeed, it is well known by those of skill in the electrophysiological arts that this step of the method can result in the use of unfortunate language by the investigator. Also, this method is not easily adapted to the manufacture of more than one harp at a time. In addition, this method results in harps that exhibit substantially uneven spacing and deviation from parallel to the base of the "U".

It is clear, then, that a novel method for the manufacture of electrophysiology harps that alleviates both the inconvenience of the temporary strand securing step of the prior art method, the inability to simultaneously manufacture a plurality of harps, and the uneven spacing and deviation from parallel would be well-appreciated by electrophysiologists.

OBJECTS OF THE INVENTION

It is an object of this invention to provide an apparatus and method for manufacturing electrophysiology harps that is faster and/or more convenient than the apparatus and method available in the prior art.

It is an additional object of this invention to provide an apparatus and method for manufacturing electrophysiology harps that allows for the manufacture of more than one harp substantially simultaneously.

It is a further object of this invention to provide an apparatus and method for manufacturing electrophysiology harps that allows for the manufacture of harps that exhibit substantially evenly spaced and substantially parallel strands.

It is further still an object of this invention to provide an electrophysiology harp that exhibits substantially evenly spaced and substantially parallel strands.

SUMMARY OF THE INVENTION

Consistent with the present invention is a jig for the manufacture of electrophysiology harps containing a top surface upon which may be placed one or more "U"s and two arrays of strand-securing notches, wherein the arrays of notches are situated one on each of two opposing edges of the top surface of the jig. Also consistent with the present invention is a method for the manufacture of electrophysiology harps exhibiting the steps of placing "U"s on the top surface of such a jig, stringing one or more strands across the "U"s such that points of contact form between the strands and the "U"s, securing the strands in the notches, cementing the points of contact, and severing the strands just distal to the points of contact. Additionally consistent with the present invention is an electrophysiology harp with strands that are substantially parallel to one another and/or equidistant from one another.

BRIEF DESCRIPTION OF THE DRAWINGS

Other objects and advantages of the present invention will become apparent from the following more detailed description of the invention taken in conjunction with the attached drawings in which.

DETAILED DESCRIPTION OF THE INVENTION

Figure 1:
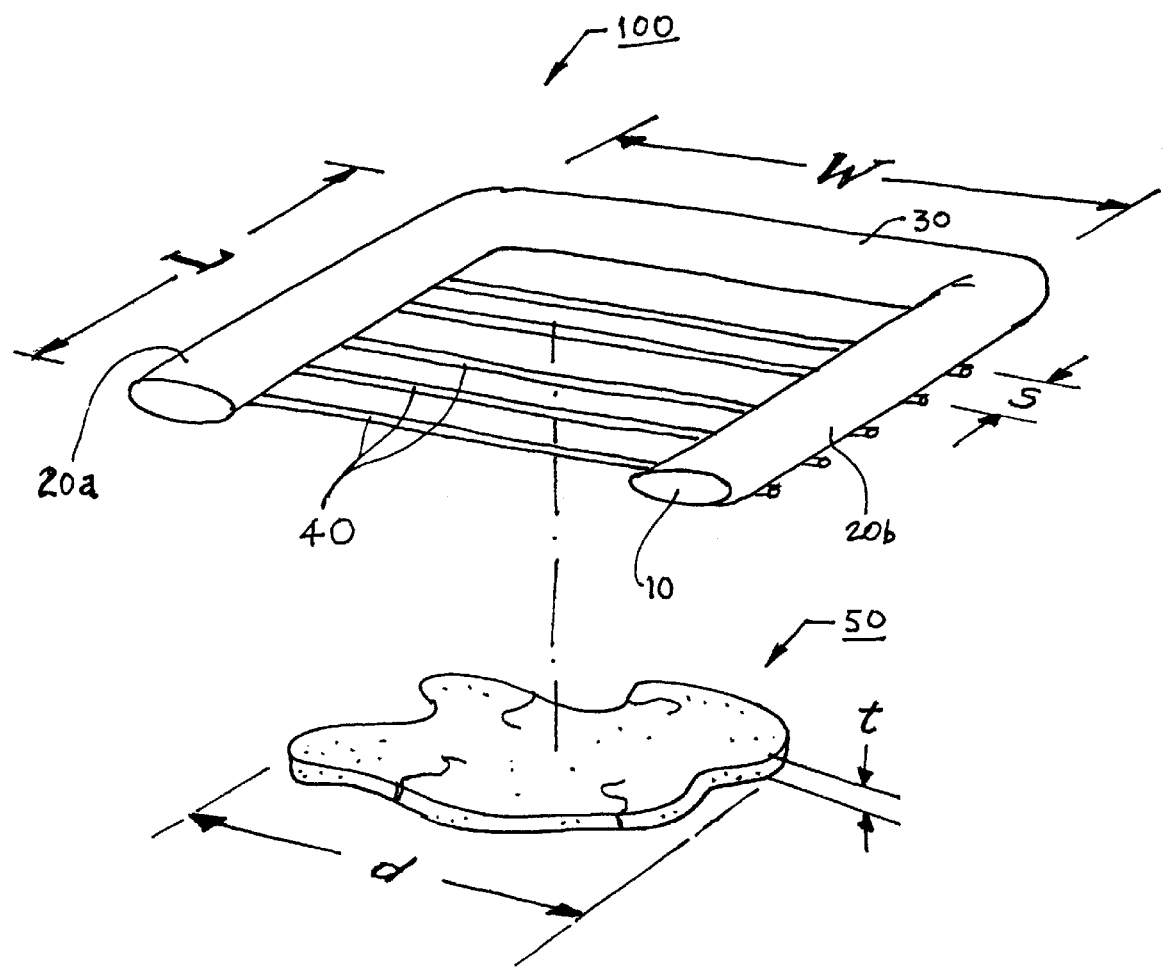
FIG. 1 is a schematic drawing of an electrophysiology harp as known in the prior art.
Figure 2:
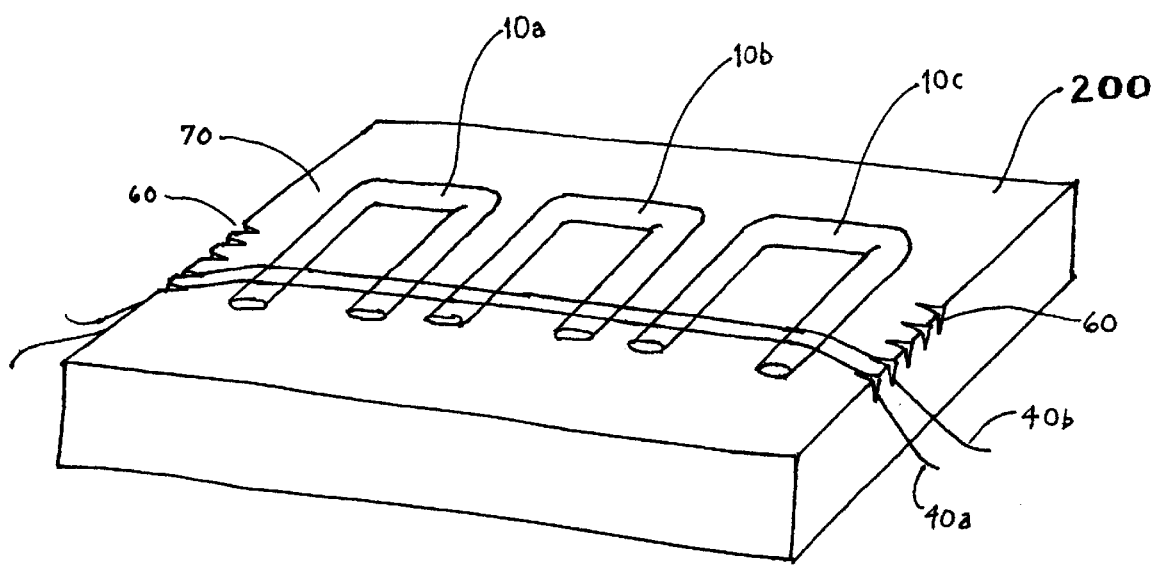
FIG. 2 is a schematic perspective view of an apparatus for the manufacture of electrophysiology harps that is an embodiment of the present invention.
Figure 3:
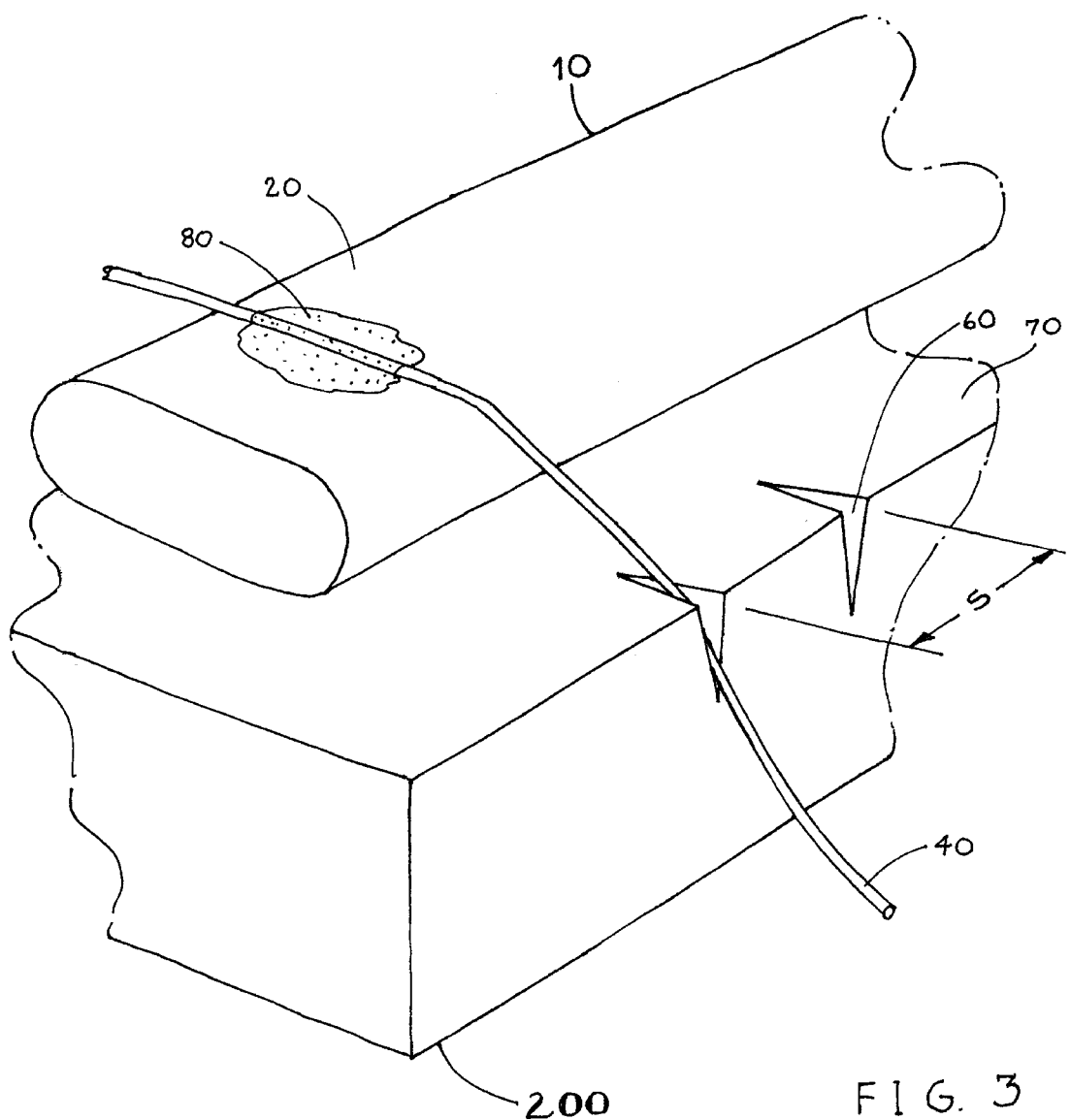
FIG. 3 is a close-up schematic perspective view of the notch-containing portion of an apparatus for the manufacture of electrophysiology harps that is an embodiment of the present invention.

An embodiment of the present invention is depicted in FIGS. 2 and 3. The "U"s 10 and the strands 40 are the workpieces that are manipulated on the jig 200 that is an embodiment of the present invention. In the disclosed embodiment, the jig 200 is a solid or laminated piece of material (for example plastic, wood, or metal) upon the top surface 70 of which one or more already-flattened "U"s 10 are lined up as shown in FIG. 2. The "U"s are to be lined up such that the arms 20 are substantially parallel with the array of notches 60 on each opposing side of the jig. It is preferred, although required, that the top surface 70 of the jig 200 be manufactured from a material (such as Teflon™) to which "superglue"-type cement will not strongly adhere. The flattened "U"s 10 may be prepared using the prior art method described above. Then the strands 40 are strung across the jig 200, over and in contact with the "U"s 10. Each strand's ends are secured by being pulled into a pair of opposed notches 60. While FIG. 2 depicts five opposed notches 60, any desired number of notches may be used (depending on both the size of the "U"s and the desired spacing s of the strands). All of the strands 40 will be parallel and equidistant from one another if the notches on each opposing side of the jig are arrayed with the same spacing s, but this is not a requirement of the present invention, although it is certainly consistent with the present invention.

A notch 60 with a strand end secured therein is depicted in a close up view in FIG. 3. The notch 60 has a depth, width, and shape such that the strand 40 will be held by a "friction fit" between the two opposing walls when it is pulled by the user of the jig 200 downwards relative to the surface of the jig 200 upon which the "U" 10 rests. Such notches for securing flexible strands, strings, or ropes are well known in the mechanical arts. Once all of the strands 40 have been secured in the notches 60, the user of the jig applies a droplet 80 of "superglue"-type cement to each of the points of contact between the strands 40 and the "U"s 10, as in the prior art method.

Once each of the droplets 80 have dried, the strand ends are severed just distal to the points of contact with the "U"s, as in the prior art method. The completed harps may then be removed from the jig and put to their intended use. As explained above, if the jig 200 is manufactured so that the notches 60 are arrayed with substantially identical equidistant spacing on each opposing side of the jig, then the completed harps, unlike harps manufactured using the prior art method, will have substantially parallel strands with substantially identical spacing between each strand and its neighbors. The use of a material for the construction of the top surface of the jig to which "superglue"-type cement will not strongly adhere allows for easy clean up of any glue that inadvertently drips on the jig during manufacture of the harps.

This description of an embodiment of the present invention is intended to be exemplary, and not to limit the invention as claimed herein.

I claim:

1. A jig for the manufacture of electrophysiology harps from "U"s and strands comprising:

a top surface upon which may be placed one or more "U"s, and two arrays of strand-securing notches, wherein one of said arrays is situated on each of two opposing edges of said top surface.

2. A jig as in claim 1, wherein said top surface is manufactured from a material to which "superglue"-type cement does not strongly adhere.

3. A jig as in claim 1, wherein said strand-securing notches are substantially identically equidistantly spaced within said two arrays.

4. A jig as in claim 1, wherein said top surface is large enough for the placement of more than one "U".

5. A method for the manufacture of one or more electrophysiology harps from "U"s and strands comprising the steps of:

placing one or more "U"s on a top surface of a jig with arrays of notches on opposing edges of said top surface, stringing one or more strands across the "U"s such that points of contact form between the strands and the "U"s, securing the strands in said notches, cementing said points of contact, and severing the strands just distal to each of said points of contact.

6. A method as in claim 5, wherein said arrays of notches are substantially identically equidistantly spaced.

7. A method as in claim 5, wherein more than one electrophysiology harp is manufactured substantially simultaneously.

* * * * *